United States Patent
Uehara et al.

(10) Patent No.: US 7,244,595 B2
(45) Date of Patent: Jul. 17, 2007

(54) METHOD OF MAINTAINING OR IMPROVING A NITRILE HYDRATASE ACTIVITY

(75) Inventors: Yoshikazu Uehara, Takaishi (JP); Masako Suehiro, Takaishi (JP); Takeshi Fukuda, Takaishi (JP); Isao Fukada, Takaishi (JP)

(73) Assignee: Mitsui Chemicals, Inc., Tokyo (JP)

( * ) Notice: Subject to any disclaimer, the term of this patent is extended or adjusted under 35 U.S.C. 154(b) by 427 days.

(21) Appl. No.: 10/850,374

(22) Filed: May 21, 2004

(65) Prior Publication Data

US 2005/0014243 A1 Jan. 20, 2005

(30) Foreign Application Priority Data

May 28, 2003 (JP) ............................. 2003-151214

(51) Int. Cl.
*C12P 13/02* (2006.01)
*C12N 9/88* (2006.01)
*C12N 1/20* (2006.01)

(52) U.S. Cl. .................. 435/129; 435/232; 435/252.33

(58) Field of Classification Search ................ 435/232, 435/129, 252.33
See application file for complete search history.

(56) References Cited

U.S. PATENT DOCUMENTS

| | | | | |
|---|---|---|---|---|
| 5,179,014 A | * | 1/1993 | Watanabe et al. | 435/129 |
| 5,705,382 A | * | 1/1998 | Endo et al. | 435/260 |
| 6,132,985 A | * | 10/2000 | Pierce | 435/29 |
| 6,316,242 B1 | * | 11/2001 | Endo et al. | 435/232 |

FOREIGN PATENT DOCUMENTS

| | | |
|---|---|---|
| DE | 43 13 649 C1 | 1/1995 |
| EP | 0 707 061 A1 | 4/1996 |

OTHER PUBLICATIONS

M. Odaka; M. Tsujimura; and I. Endo, "Post-translational modifications in nitrile hydrates family", RIKEN Review No. 41, Nov. 20001, pp. 58-60.

O. Masafumi, T. Masanari; and I. Endo, "Structure and function of iron-type nitrile hydratases: an inhibition study", New Development of Reaction in Organic Chemistry, No. 3, 2001, pp. 17-20.

P. K. Mascharak, "Structural and functional models of nitrile hydratase", Coordination Chemistry Reviews, No. 225, 2002, pp. 201-214.

Patent Abstract of Japan 05-043351, Date of Publication Jul. 1, 1993 (cited in specification).

Patent Abstract of Japan 04-048435, Date of Publication Aug. 6, 1992 (cited in specification).

Patent Abstract of Japan 08-112089, Date of Publication May 7, 1996 (cited in specification).

Patent Abstract of Japan 02-000035, Date of Publication Jan. 5, 1990 (cited in specification).

Patent Abstract of Japan 2002-017339, Date of Publication Jan. 22, 2002 (cited in specification).

Nojiri et al., "Cobalt-substituted Fe-type nitrile hydratase of *Rhodococcus* sp. N-771," *FEBS Letters*, Jan. 14, 2000, pp. 173-177, vol. 465, No. 2-3, Elsevier Science Publishers, Amsterdam, NL.

Search Report dated Aug. 4, 2005 in corresponding French Application No. 0405712000.

* cited by examiner

*Primary Examiner*—Herbert J. Lilling
(74) *Attorney, Agent, or Firm*—Buchanan Ingersoll & Rooney PC

(57) ABSTRACT

The object of this invention is to provide a method which not only maintains the nitrile hydratase activity of a nitrile hydratase-containing cell or a treated material of the cell under conditions where the cell does not grow, but also improves the nitrile hydratase activity of a nitrile hydratase-containing cell or a treated material of the cell whose activity was once reduced. This invention relates to a method of maintaining or improving a nitrile hydratase activity which comprises bringing a nitrile hydratase-containing cell or a treated material of the cell into contact with an oxidizing agent under conditions where the cell does not grow, as well as a method of producing an amide compound from a nitrile compound, which comprises using the cell brought into contact with an oxidizing agent or a treated material of the cell.

2 Claims, No Drawings

METHOD OF MAINTAINING OR IMPROVING A NITRILE HYDRATASE ACTIVITY

This application claims priority under 35 U.S.C. § 119 to Application No. 2003-151214, filed in Japan on May 28, 2003; the entire content of which is hereby incorporated by reference.

BACKGROUND OF THE INVENTION

1. Field of the Invention

The present invention relates to a method of maintaining or improving the activity of industrially useful nitrile hydratase. The activity referred to herein is a nitrile hydrating activity determined by a method described in the Examples.

2. Description of the Related Art

The nitrile hydrating activity of nitrile hydratase is unstable and easily reduced with time. For preventing such reduction in the nitrile hydrating activity of nitrile hydratase with time in the activity, a method which comprises adding at least one compound selected from a nitrile, an amide, an organic acid and a salt thereof as a stabilizer to a suspension or solution of a nitrile hydratase-containing microorganism or a treated material of the microorganism is disclosed (see, for example, JP-B 5-43351 and JP-B 4-48435).

A storage method wherein a microorganism or a treated microbial material is in a state suspended in an aqueous medium and the aqueous medium is neutral or weakly basic and having dissolved therein an inorganic salt at a concentration of 100 mM to its saturated concentration is also disclosed (see, for example, JP-A 8-112089). However, both the methods are effective only in maintaining a nitrile hydratase activity, and an effect of further increasing the nitrile hydratase activity is not reported therein.

As a method of increasing a nitrile hydrating activity by producing a nitrile hydratase-containing microorganism through culture and then subjecting the resulting microorganism or a treated material of the microorganism to some treatment, a method which comprises irradiating the resulting Gram-positive microorganism having a nitrile hydratase activity with light is disclosed (see, for example, JP-B2-35). However, this method is effective only in increasing the nitrile hydratase activity of the microorganism obtained through culture, and does not improve the nitrile hydratase activity of a microorganism whose activity was reduced. In addition, this method is irrelevant to maintenance of nitrile hydratase activity.

It is also reported that oxygen is necessary for culturing a nitrile hydratase-containing microorganism, and the concentration of dissolved oxygen during culture is maintained in the range of from 1 ppm to its saturated concentration, whereby the growth of the microorganism can be improved, and simultaneously the microorganism expressing a nitrile hydratase activity at high levels can be obtained (see, for example, JP-A 2002-17339). However, it is merely reported in this method that during culture, that is, under conditions where the nitrile hydratase-containing microorganism grows, there is the optimum concentration of dissolved oxygen in a culture solution in order to express a nitrile hydratase activity, and there is no description therein of maintenance and improvement of the nitrile hydratase activity under conditions where the nitrile hydratase-containing microorganism does not grow, that is, after the conclusion of culture.

The detailed mechanism of expression and reduction of nitrile hydratase activity is not completely elucidated, but it is described that for example, the reduction of the nitrile hydrating activity of iron-type nitrile hydratase derived from *Rhodococcus* sp. N-771 is attributable to oxidation, with oxygen in the air, of cysteinesulfenic acid coordinated with non-heme iron (III) as central metal into cysteinesulfinic acid (see, for example, M. Okada, M. Tsujimura and I. Endo: RIKEN Review, No. 41, p. 58-60 (2001)).

It is also described that for example, the activity of iron-type nitrile hydratase derived from *Rhodococcus* sp. N-771 is lost when trivalent iron as central metal is reduced to divalent iron by 2-cyano-2-propylhydroxy peroxide while cysteinesulfenic acid is oxidized into cysteinesulfinic acid (see, for example, M. Okada, M. Tsujimura and I. Endo: New Development of Reaction in Organic Chemistry (in Japanese), No. 3, p. 17-20 (2001).

It is also described that the structure of nitrile hydratase with cobalt as central metal, derived from *Rhodococcus rhodochrous* J1, is not determined, but is estimated to be similar to that of iron nitrile hydratase (see, for example, P. K. Mascharak, Coordination Chemistry Reviews, No. 225, p. 201-214 (2002)).

SUMMARY OF THE INVENTION

The object of the present invention is to provide a method which not only maintains the nitrile hydratase activity of a nitrile hydratase-containing cell or a treated material of the cell under conditions where the cell does not grow, but also improves the nitrile hydratase activity of a nitrile hydratase-containing cell or a treated material of the cell whose activity was once reduced.

The present inventors made extensive study to solve the problem, and as a result, we found that the nitrile hydratase activity of a nitrile hydratase-containing cell or a treated material of the cell can be maintained by bringing it into contact with an oxidizing agent under conditions where the cell does not grow, and further the nitrile hydratase activity of a nitrile hydratase-containing cell or a treated material of the cell whose activity was once reduced can be improved by bringing it into contact with an oxidizing agent before or during reaction, and the present invention was thereby arrived at.

That is, the present invention provides:

(1) A method of maintaining or improving a nitrile hydratase activity, which comprises bringing a nitrile hydratase-containing cell or a treated material of the cell into contact with an oxidizing agent under conditions where the cell does not grow.

(2) The method of maintaining or improving a nitrile hydratase activity according to the above-mentioned (1), wherein the oxidizing agent is an oxidizing agent having a standard electrode potential in the range of 0.1 to 2.1 V relative to a standard hydrogen electrode.

(3) The method of maintaining or improving a nitrile hydratase activity according to the above-mentioned (1), wherein the oxidizing agent is at least one member selected from the group consisting of oxygen, hydrogen peroxide, potassium ferricyanide and ammonium persulfate.

(4) The method of maintaining or improving a nitrile hydratase activity according to the above-mentioned (3), wherein the oxygen as the oxidizing agent is supplied as an oxygen-containing gas.

(5) The method of maintaining or improving a nitrile hydratase activity according to the above-mentioned (1), wherein the concentration of the oxidizing agent is in the range of 1 ppm by weight to 10% by weight.
(6) The method of maintaining or improving a nitrile hydratase activity according to the above-mentioned (1), wherein the temperature in contact with the oxidizing agent is in the range of 0 to 60° C.
(7) The method of maintaining or improving a nitrile hydratase activity according to the above-mentioned (1), wherein the pH value in contact with the oxidizing agent is in the range of 5 to 10.
(8) The method of maintaining or improving a nitrile hydratase activity according to the above-mentioned (1), wherein the nitrile hydratase is a nitrile hydratase containing cobalt in its molecule.
(9) The method of maintaining or improving a nitrile hydratase activity according to the above-mentioned (1), wherein a cell where the nitrile hydratase containing cobalt in its molecule is expressed by genetic recombination, or a treated material of the cell, is brought into contact with the oxidizing agent under conditions where the cell does not grow.
(10) The method of maintaining or improving a nitrile hydratase activity according to the above-mentioned (1), wherein the cell is a nitrile hydratase-containing microorganism or a treated material of the microorganism.
(11) The method of maintaining or improving a nitrile hydratase activity according to the above-mentioned (10), wherein the microorganism is a genetically engineered microorganism.
(12) The method of maintaining or improving a nitrile hydratase activity according to the above-mentioned (11), wherein the genetically engineered microorganism is genetically engineered *Escherichia coli*.
(13) The method of maintaining or improving a nitrile hydratase activity according to the above-mentioned (12), wherein a host of the genetically engineered *Escherichia coli* is W3110 strain (ATCC27325), HB101 strain (ATCC33694), JM109 strain (ATCC53223) or WA802 strain (ATCC33526), each of which is derived from *Escherichia coli* K-12.
(14) The method of maintaining or improving a nitrile hydratase activity according to the above-mentioned (1), wherein the nitrile hydratase-containing cell or a treated material of the cell is used for producing an amide compound from a nitrile compound.
(15) A method of producing an amide compound from a nitrile compound, which comprises contacting a nitrile compound with the nitrile hydratase-containing cell or a treated material of the cell obtained by the method described in any one of the above-mentioned (1) to (14).

DETAILED DESCRIPTION OF THE INVENTION

Hereinafter, the present invention is described in more detail. The nitrile hydratase referred to in the present invention is an enzyme having an ability to hydrate a nitrile group of a nitrile compound to form the corresponding amide compound. The cell referred to in the present invention may be any one of microorganisms, plant cells and animal cells. The nitrile hydratase-containing microorganism is not particularly limited insofar as it is a microorganism having an ability to hydrate a nitrile group of a nitrile compound to form the corresponding amide compound. Examples thereof include *Pseudonocardia thermophila* JCM3095, *Achromobacter xerosis* IFO12668 and *Rhodococcus rhodochrous* J1.

The present invention also encompasses a transformant wherein a nitrile hydratase gene cloned from the above microorganism is expressed in an arbitrary host. The arbitrary host includes *Escherichia coli*, microorganisms of the genus *Bacillus*, such as *Bacillus subtilis*, yeasts, *Actinomyces*, and filamentous fungi. The host of genetically engineered *Escherichia coli* includes, for example, W3110 strain (ATCC27325), HB101 strain (ATCC33694), JM109 strain (ATCC53223) and WA802 strain (ATCC33526), each of which is derived from *Escherichia coli* K-12. Concrete examples thereof include MT-10822 (which was deposited as FERM BP-5785 on Feb. 7, 1996 with the National Institute of Bioscience and Human-Technology (Higashi 1-1-3, Tsukuba City, Ibaraki Pref., JP), the Agency of Industrial Science and Technology, the Ministry of International Trade and Industry, Japan, under the Budapest Treaty on international approval of microbial deposition in patent proceedings).

A transformant expressing a mutant nitrile hydratase with further improvements in drug resistance, thermostability etc. by replacement of one or more constitutional amino acids of the enzyme by other amino acids or by deletion, elimination or insertion of one or more constitutional amino acids by recombinant DNA technology also falls under the scope of the invention.

The microorganism of the present invention is prepared usually by utilizing general methods known in molecular biology, biological engineering, and genetic engineering. For example, the microorganism is inoculated usually into a liquid medium such as LB medium or M9 medium and allowed to grow at a suitable culture temperature (which is generally 20 to 50° C., but may be 50° C. or more for thermophilic bacteria), and then the microorganism is separated from the culture liquid by centrifugation etc., to give the microorganism of the present invention.

The treated material in the present invention refers to an extract or a trituration material of the microorganism, a separated material obtained by separating and purifying an active fraction of nitrile hydratase from the extract or the trituration material, and an immobilized material obtained by immobilizing the cell, or the extract, the trituration material of the cell or the separated material onto a suitable carrier, and these materials correspond to the treated material of the cell of the present invention insofar as they have a nitrile hydratase activity. These materials may be used alone, or simultaneously or alternately in two or more different forms.

In the present invention, the conditions where the cell does not grow include, for example, those conditions where the cell or a treated material of the cell is dissolved or suspended in water, physiological saline, or an aqueous solution containing a buffer such as phosphate, an inorganic salt such as sulfate or carbonate, an alkali metal hydroxide or an amide compound dissolved therein at a suitable concentration. The aqueous solution also includes a reaction solution for producing an amide compound from a nitrile compound by the cell or the treated material of the cell. The aqueous solution further includes a culture solution in which the microorganism is cultured or a culture solution after the resting phase of growth of the microorganism or after the conclusion of culture. In addition, the aqueous solution includes a culture solution sterilized with a chemical or by heating.

The oxidizing agent used in the present invention is an organic or inorganic substance having a standard electrode potential in the range of 0.1 to 2.1 V relative to a standard hydrogen electrode. A substance of less than 0.1 V has less ability as an oxidizing agent and is thus poor in the effect of maintaining and activating a nitrile hydratase activity. A substance of higher than 2.1 V has too strong ability as an oxidizing agent, thus causing deterioration of nitrile hydratase significantly and adversely reducing a nitrile hydratase activity. Examples of the oxidizing agent are listed in "Kagaku Binran" (Chemical Handbook) edited by The Chemical Society of Japan, and from the listed substances, one substance may be used, or two or more substances may be used simultaneously or alternately. Examples of such substances include oxygen, hydrogen peroxide, potassium ferricyanide, persulfate, permanganate, periodate, perchloric acid, perchlorate, nitric acid, nitrate, cerium (IV) salt, etc. Preferably, oxygen, hydrogen peroxide, potassium ferricyanide or ammonium persulfate is used as the oxidizing agent. More preferably, pure oxygen, or oxygen in the air, is supplied.

In the present invention, a nitrile hydratase-containing cell or the treated material of the cell is brought into contact with the oxidizing agent under conditions where the cell does not grow, and the oxidizing agent may be brought into contact with the cell or a treated material of the cell in one portion or successively.

In contact with oxygen as the oxidizing agent, an oxygen-containing gas is supplied. The gas supplied may be the air, pure oxygen, a gas containing the air and nitrogen or another gas mixed in a predetermined ratio, or a gas containing oxygen and nitrogen or another gas mixed in a predetermined ratio. Another gas referred to herein may be a single kind of gas such as nitrogen, argon or helium, or a mixture of two or more kinds of gas, and is not particularly limited insofar as it does not inhibit the reaction. For example, when the cell or a treated material of the cell is suspended in an aqueous medium in a stirring container, oxygen can be dissolved in the aqueous medium under stirring by supplying the gas into a gaseous phase in the stirring container while purging the gaseous phase. Alternatively, the gas can be dispersed and diffused by a sparger to supply oxygen in a larger gas/liquid contact area under stirring. The gas is supplied preferably after removal of miscellaneous germs by a filter for removing germs, whereby the decay of the suspension by contamination with miscellaneous germs can be prevented.

In the present invention, the cell or a treated material of the cell may be contacted as such with the oxidizing agent, but is usually contacted in the form of a suspension in an aqueous medium with the oxidizing agent. As used herein, the aqueous medium is a water-containing medium, and refers to physiological saline, an aqueous solution containing a buffer such as phosphate, an inorganic salt such as sulfate or carbonate, an alkali metal hydroxide, or an amide compound dissolved therein at a suitable concentration, a reaction solution for producing an amide compound from a nitrile compound, and a culture solution after the resting phase.

The concentration of the cell or a treated material of the cell upon suspension in an aqueous medium is not particularly limited, but may be usually in the range of 0.1 to 30% by weight (based on the dry weight of the cell) in the aqueous medium.

When the oxidizing agent is brought into contact with the nitrile hydratase-containing cell or a treated material of the cell in the present invention, the concentration of the oxidizing agent is not particularly limited insofar as it is a concentration at which the nitrile hydratase activity can be maintained or improved, but preferably, the concentration is in the range of 1 ppm by weight to 10% by weight in the aqueous medium.

When the oxidizing agent is brought into contact with the nitrile hydratase-containing cell or a treated material of the cell in the present invention, the temperature is usually 0 to 60° C., preferably 0 to 50° C., more preferably 5 to 40° C. During contact, the pH value is usually 5 to 10, preferably 5 to 9, still more preferably 6 to 8.

According to the present invention, the nitrile hydratase activity of a nitrile hydratase-containing cell or a treated material of the cell can be maintained under conditions where the cell does not grow, by bringing it into contact with an oxidizing agent, and further the nitrile hydratase activity of a cell whose nitrile hydratase activity has been once reduced or a treated material of the cell can be improved by bringing it into contact with an oxidizing agent before or during the reaction. Accordingly, the contact of the nitrile hydratase-containing cell or a treated material of the cell with the oxidizing agent can be carried out at an arbitrary point in time before the conclusion of the nitrile hydration reaction.

That is, the microorganism or a treated material of the microorganism may be brought into contact with the oxidizing agent before the hydration reaction, or the microorganism or a treated material of the microorganism may first be subjected to the reaction and then the oxidizing agent is subjected to the reaction thus bringing it into contact with the microorganism or a treated material of the microorganism. However, when the oxidizing agent is subjected to the reaction, side reactions different from the hydration reaction of a nitrile compound may occur; for example, when the nitrile compound is (meth)acrylonitrile, the nitrile compound itself or its corresponding product (meth)acrylamide may be polymerized, and it is therefore preferable that before the reaction, the microorganism or a treated material of the microorganism is brought into contact with the oxidizing agent.

After the culture is finished, the microorganism itself or the treated microbial material is brought into contact with the oxidizing agent to improve a nitrile hydrating activity based on nitrile hydratase, and then the microorganism or the treated microbial material can be subjected as such to the reaction, but may if necessary be washed and then subjected to the reaction. For example, when the microorganism or the treated microbial material in the form of a suspension in aqueous medium is brought into contact with oxygen as the oxidizing agent, an improvement in the nitrile hydrating activity is confirmed, and thereafter, the nitrile hydrating activity can be maintained even if the dissolved oxygen in the aqueous medium is removed by passage of nitrogen, and thus the microorganism or the treated microbial material can be subjected in this state to the reaction.

The nitrile compound in the present invention is a nitrile compound having about 2 to 20 carbon atoms, which includes, but is not limited to, nitriles such as aliphatic nitrile and aromatic nitrile. The aliphatic nitrile includes a saturated or unsaturated nitrile having 2 to 6 carbon atoms, for example aliphatic saturated mononitriles such as acetonitrile, propionitrile, butyronitrile, isobutyronitrile, valeronitrile, isovaleronitrile and capronitrile; aliphatic saturated dinitriles such as malononitrile, succinonitrile and adiponitrile; and aliphatic unsaturated nitrites such as acrylonitrile, methacrylonitrile and crotononitrile.

The aromatic nitrile includes benzonitrile, o-, m- and p-chlorobenzonitrile, o-, m- and p-fluorobenzonitrile, o-, m- and p-nitrobenzonitrile, o-, m- and p-tolunitrile, benzyl cyanide etc. In particular, acrylonitrile, methacrylonitrile, and crotononitrile can be mentioned as preferable examples.

EXAMPLES

Hereinafter, the present invention is described in more detail by reference to the Examples, but the present invention is not limited by the following examples. In HPLC analysis of a reaction solution in the Examples, ULTRON 80HG (50×8 φmm) was used as an HPLC column, and 10 mM aqueous phosphate solution was used as a developing solution. Acrylamide and acrylonitrile were detected by absorbance at 220 nm to determine their concentrations. The concentration of dissolved oxygen was measured by an oxygen electrode (InPro 6800/12/320 manufactured by Mettler-Toledo K.K.) and an dissolved oxygen concentration indicator (4050e model manufactured by Mettler-Toledo K.K.), after it was calibrated that 0 was indicated with 5% aqueous sodium sulfite and 10.92 ppm was indicated by saturation oxygen concentration in pure water at 10° C. previously saturated with the air.

Example 1

MT-10822 strain (FERM BP-5785, see JP-A 11-253168) having a nitrile hydratase gene introduced into *Escherichia coli* HB101, deposited by Mitsui Chemicals, Inc., was used as the nitrile hydratase-containing cell in this example.

For culture of this microbial strain, 15.0 L medium having the following composition was prepared in a 30 L culture container and sterilized with high-pressure steam at 121° C. for 20 minutes. Ampicillin was added at a final concentration of 50 μg/ml to this medium, and the microbial strain was inoculated via a platinum loop thereto and cultured at 37° C. at 700 rpm for 20 hours. About 15 hours after the culture was initiated, IPTG (isopropyl-β-D-thiogalactopyranoside) was added at a final concentration of 100 μmol/L, and the culture was continued.

| (Medium composition) | |
|---|---|
| Yeast extract | 5.0 g/L |
| Polypeptone | 10.0 g/L |
| NaCl | 5.0 g/L |
| Cobalt chloride•6H2O | 10.0 mg/L |
| Ferric sulfate•7H2O | 40.0 mg/L |
| pH 7.5 | |

After the culture was finished, 500 mL microbial suspension wherein microbial growth had been terminated was transferred to a 1 L flask equipped with an oxygen electrode and a thermometer. The suspension was kept at 10° C. under stirring, while the air (400 N-ml/min.) was passed through the gaseous phase in the flask. 0 hour and 24 hours after storage, a part of the microbial suspension was removed. During this storage, the concentration of dissolved oxygen in the microbial suspension indicated 10.0 to 10.9 ppm.

The microbial suspension, 23.0 mg, was suspended in 10.0 g of previously deoxidized 50 mM Tris-HCl buffer (pH 8.1) in a 100 ml sealable glass container previously sufficiently purged with nitrogen, and previously deoxidized acrylonitrile was added at a final concentration of 19% by weight to this suspension and reacted at 20° C. for 2 hours under stirring. The reaction was terminated by adding 80 g of 10 mM aqueous phosphoric acid, and then the concentration of acrylamide in the reaction solution was determined by HPLC analysis. Subsequently, the concentration of the microbial suspension was determined on the basis of the dry weight of the microorganism, and then the amount of formed acrylamide per unit dry weight of the microorganism was calculated. Assuming that the amount of acrylamide formed in 0 hour of storage was 1, the amount of formed acrylamide was 1.1 in the 24th hour of storage, indicating that the nitrile hydratase activity of the nitrile hydratase was maintained stably during the storage.

Example 2

500 mL microbial suspension wherein microbial growth had been terminated, obtained in the same manner as in Example 1, was transferred to a 1 L flask equipped with an oxygen electrode and a thermometer. The suspension was kept at 10° C. under stirring, while a mixture of the air (400 N-ml/min.) and nitrogen (4000 N-ml/min.) was passed through the gaseous phase in the flask. 0 hour and 24 hours after storage, a part of the microbial suspension was removed. During this storage, the concentration of dissolved oxygen in the microbial suspension indicated 1.0 to 1.5 ppm. The amount of formed acrylamide in the microbial suspension per unit dry weight of the microorganism was determined in the same manner as in Example 1. Assuming that the amount of acrylamide formed in 0 hour of storage was 1, the amount was 1.0 in the 24th hour, indicating that the nitrile hydrating activity of the nitrile hydratase was kept stably during the storage.

Comparative Example 1

500 mL microbial suspension wherein microbial growth had been terminated, obtained in the same manner as in Example 1, was transferred to a 1 L flask equipped with an oxygen electrode and a thermometer. The suspension was kept at 10° C. under stirring, while nitrogen (400 N-ml/min.) was passed through the gaseous phase in the flask to deoxidize the microbial suspension under stirring. 0, 1 and 3 hours after storage, apart of the microbial suspension was removed. During this storage, the concentration of dissolved oxygen in the microbial suspension indicated 0.0 ppm. The amount of formed acrylamide in the microbial suspension per unit dry weight of the microorganism was determined in the same manner as in Example 1. Assuming that the amount of acrylamide formed in 0 hour of storage was 1, the amount was 0.45 in the first hour and 0.20 in the 3rd hour, indicating that the nitrile hydrating activity of the nitrile hydratase was reduced with time during the storage.

Comparative Example 2

500 mL microbial suspension wherein microbial growth had been terminated, obtained in the same manner as in Example 1, was transferred to a 1 L flask equipped with an oxygen electrode and a thermometer. The suspension was kept at 10° C. under stirring, while nitrogen (400 N-ml/min.) was passed through the gaseous phase in the flask. The amount of formed acrylamide in 0 hour of storage in the microbial suspension per unit dry weight of the microorganism was determined in the same manner as in Example 1. 1 hour after storage, a part of the microbial suspension was removed and centrifuged (15000 G×13 minutes) in a nitrogen atmosphere to separate the microorganism only from the suspension to give a wet microorganism.

The resulting microorganism, 0.20 g, was suspended in previously deoxidized pure water in a 100 ml sealable glass container previously sufficiently purged with nitrogen, to give 20.00 g suspension. The microbial suspension was kept at 20° C. for 15 minutes under stirring.

The microbial suspension, 66.0 mg, was suspended in 10.0 g of previously deoxidized 50 mM Tris-HCl buffer (pH 8.1) in a 100 ml sealable glass container previously sufficiently purged with nitrogen, and previously deoxidized acrylonitrile was added at a final concentration of 19% by weight to this suspension and reacted at 20° C. for 4 hours under stirring. The reaction was terminated by adding 80 g of 10 mM aqueous phosphoric acid, and then the concentration of acrylamide in the reaction solution was determined by HPLC analysis. Subsequently, the concentration of the microbial suspension based on the dry weight of the microorganism was determined, and then the amount of formed acrylamide per unit dry weight of the microorganism was calculated. Assuming that the amount of acrylamide formed after 1 hour of storage by the wet microorganism obtained by centrifugation was 1.0, the amount of formed acrylamide was 2.9 in 0 hour of storage, and it was thus confirmed that the nitrile hydratase activity of the wet microorganism obtained in Comparative Example 2 was reduced.

Examples 3 to 9

A microbial suspension wherein microbial growth had been terminated, obtained in the same manner as in Example 1, was centrifuged (15000 G×15 minutes) to separate the microorganism only from the suspension to give a wet microorganism. The resulting microorganism, 0.20 g, was suspended in previously deoxidized pure water in a 100 ml sealable glass container previously sufficiently purged with nitrogen, and potassium ferricyanide was added and suspended as an oxidizing agent at a final concentration shown in Table 1 to give 20.00 g suspension. Separately, an oxidizing agent-free microbial suspension was prepared in the same manner. The microbial suspension was kept at 20° C. for 15 minutes under stirring.

The microbial suspension, 66.0 mg, was suspended in 10.0 g of previously deoxidized 50 mM Tris-HCl buffer (pH 8.1) in a 100 ml sealable glass container previously sufficiently purged with nitrogen, and previously deoxidized acrylonitrile was added at a final concentration of 19% by weight to this suspension and reacted at 20° C. for 4 hours under stirring. The reaction was terminated by adding 80 g of 10 mM aqueous phosphoric acid, and then the concentration of acrylamide in the reaction solution was determined by HPLC analysis. Subsequently, the concentration of the microbial suspension based on the dry weight of the microorganism was determined, and then the amount of formed acrylamide per unit dry weight of the microorganism was calculated. Assuming that the amount of formed acrylamide per unit dry weight of the microorganism in the absence of the oxidizing agent is 1.0, the amounts of formed acrylamide in Examples 3 to 9 are shown as relative values in Table 1.

Examples 10 to 11

The amount of acrylamide formed per unit dry weight of the microorganism was determined in the same manner as in Example 3 except that in place of potassium ferricyanide, ammonium persulfate was added and suspended as an oxidizing agent at a concentration shown in Table 1. Assuming that the amount of formed acrylamide per unit dry weight of the microorganism in the absence of the oxidizing agent is 1.0, the amounts of formed acrylamide in Examples 10 to 11 are shown as relative values in Table 1.

Example 12

The amount of acrylamide formed per unit dry weight of the microorganism was determined in the same manner as in Example 3 except that in place of potassium ferricyanide, 30 wt % aqueous hydrogen peroxide was added and suspended as an oxidizing agent at a concentration shown in Table 1. Assuming that the amount of formed acrylamide per unit dry weight of the microorganism in the absence of the oxidizing agent is 1.0, the amount of formed acrylamide in Example 12 is shown as a relative value in Table 1.

TABLE 1

| | REAGENT | CONCENTRATION (WT %) | AMOUNT OF ACRYLAMIDE FORMED (RELATIVE VALUE) |
|---|---|---|---|
| — | — | NOT ADDED | 1.0 |
| EXAMPLE 3 | POTASSIUM FERRICYANIDE | 0.20 | 1.4 |
| EXAMPLE 4 | POTASSIUM FERRICYANIDE | 0.39 | 1.7 |
| EXAMPLE 5 | POTASSIUM FERRICYANIDE | 0.81 | 2.0 |
| EXAMPLE 6 | POTASSIUM FERRICYANIDE | 1.9 | 2.4 |
| EXAMPLE 7 | POTASSIUM FERRICYANIDE | 1.6 | 2.6 |
| EXAMPLE 8 | POTASSIUM FERRICYANIDE | 2.0 | 2.9 |
| EXAMPLE 9 | POTASSIUM FERRICYANIDE | 10.0 | 2.9 |
| EXAMPLE 10 | AMMONIUM PERSULFATE | 1.3 | 1.6 |
| EXAMPLE 11 | AMMONIUM PERSULFATE | 2.7 | 1.6 |
| EXAMPLE 12 | HYDROGEN PEROXIDE | 0.21 | 2.4 |

From the results shown above, it can be seen that when the microorganism is brought into contact with an oxidizing agent such as potassium ferricyanide, hydrogen peroxide or ammonium persulfate, the nitrile hydrating activity of the nitrile hydratase is improved.

Example 13

0.20 g wet microorganism obtained in the same manner as in Example 3 was suspended in previously deoxidized pure water in a 100 ml sealable glass container previously sufficiently purged with nitrogen, and potassium ferricyanide was added and suspended as an oxidizing agent at a final concentration of 0.77% by weight to give 20.00 g suspension. The microbial suspension was kept at 20° C. under stirring. 0 minute, 10 minutes, 2 hours and 24 hours after the stirring was initiated, a small amount of the microbial suspension was collected, and the amount of formed acrylamide per unit dry weight of the microorganism was determined in the same manner as in Example 3. Assuming that the amount of acrylamide formed in 0 minute of stirring by per unit dry weight of the microorganism is 1, the amounts of acrylamide formed in the 10th minute, in the second hour and in the 24th hour after initiation of stirring are shown as relative values in Table 2.

TABLE 2

| | STIRRING TIME | AMOUNT OF ACRYLAMIDE FORMED (RELATIVE VALUE) |
|---|---|---|
| EXAMPLE 13 | 0 HOUR | 1.0 |
| | 10 MINUTES | 1.7 |
| | 2 HOURS | 2.5 |
| | 24 HOURS | 2.4 |

From the results shown above, it can be seen that when the microorganism is brought into contact with an oxidizing agent such as potassium ferricyanide, the nitrile hydrating activity of the nitrile hydratase is improved depending on the contact time, and simultaneously the improved activity is maintained.

Example 14

A wet microorganism was obtained in the same manner as in Example 3. The resulting wet microorganism, 1.5 g, was suspended in 48.5 g pure water in a 100 mL flask equipped with an oxygen electrode and a thermometer. The suspension was kept at 10° C. under stirring, while the air (40 N-ml/min.) was passed through the gaseous phase in the flask. 0, 1, 2, 3, 7 and 19 days after storage, a part of the microbial suspension was removed. During this storage, the concentration of dissolved oxygen in the microbial suspension indicated 10.0 to 10.9 ppm. The amount of formed acrylamide in each of the collected microbial suspensions per unit dry weight of the microorganism was determined in the same manner as in Example 3. Assuming that the amount of acrylamide formed on 0 day of storage by per unit dry weight of the microorganism is 1, the amounts of acrylamide formed on the first day, second day, third day, seventh day and nineteenth day of storage are shown as relative values in Table 3.

Example 15

A wet microorganism was obtained in the same manner as in Example 3. The resulting wet microorganism, 1.5 g, was suspended in 48.5 g pure water in a 100 mL flask equipped with an oxygen electrode and a thermometer. The suspension was kept at 10° C. under stirring, while a mixture of the air (40 N-ml/min.) and nitrogen (400 N-ml/min.) was passed through the gaseous phase in the flask. 0, 1, 2, 3, 7 and 19 days after storage, a part of the microbial suspension was removed. During this storage, the concentration of dissolved oxygen in the microbial suspension indicated 1.0 to 1.5 ppm. The amount of formed acrylamide in each of the collected microbial suspensions per unit dry weight of the microorganism was determined in the same manner as in Example 3. Assuming that the amount of acrylamide formed on 0 day of storage by per unit dry weight of the microorganism is 1, the amounts of acrylamide formed on the first day, second day, third day, seventh day and nineteenth day of storage are shown as relative values in Table 3.

TABLE 3

| | NUMBER OF DAYS FOR STORAGE | | | | | |
|---|---|---|---|---|---|---|
| | 0 | 1 | 2 | 3 | 7 | 19 |
| EXAMPLE 14 | 1.0 | 2.4 | 2.3 | 2.4 | 2.5 | 2.5 |
| EXAMPLE 15 | 1.0 | 1.6 | 2.3 | 2.4 | 2.5 | 2.4 |

From the results shown above, it can be seen that when the microorganism is brought into contact with oxygen as the oxidizing agent, the nitrile hydrating activity of the nitrile hydratase is improved depending on the contact time, and after a predetermined time, the nitrile hydrating activity is highly and stably maintained.

Examples 16 to 18

0.20 g wet microorganism obtained in the same manner as in Example 3 was suspended in previously deoxidized pure water in a 100 ml sealable glass container previously sufficiently purged with nitrogen, and potassium ferricyanide was added and suspended as an oxidizing agent at a final concentration of 2.0% by weight, and the suspension was adjusted with an aqueous sodium hydroxide solution or sulfuric acid to a pH value shown in Table 4 to give 20.00 g suspension. Separately, a microbial suspension wherein the oxidizing agent was not added and the pH value was not adjusted was also prepared in the same manner. The microbial suspension was kept at 20° C. for 15 minutes under stirring. The amount of formed acrylamide per unit dry weight of the microorganism was determined in the same manner as in Example 3. Assuming that the amount of acrylamide formed per unit dry weight of the microorganism in the case where the oxidizing agent was not added and the pH value was not regulated is 1, the amounts of acrylamide formed in Examples 16 to 18 are shown as relative values in Table 4.

TABLE 4

| | REAGENT | BUFFER SOLUTION PH | AMOUNT OF ACRYLAMIDE FORMED (RELATIVE VALUE) |
|---|---|---|---|
| — | NOT ADDED | NOT REGULATED (7.1) | 1.0 |
| EXAMPLE 16 | POTASSIUM FERRICYANIDE | 5.0 | 1.8 |
| EXAMPLE 17 | POTASSIUM FERRICYANIDE | 6.7 | 2.9 |
| EXAMPLE 18 | POTASSIUM FERRICYANIDE | 10.0 | 2.0 |

Examples 19 to 21

0.20 g wet microorganism obtained in the same manner as in Example 3 was suspended in previously deoxidized pure water in a 100 ml sealable glass container previously sufficiently purged with nitrogen, and potassium ferricyanide was added and suspended as an oxidizing agent at a final concentration of 2.0% by weight to give 20.00 g suspension. Separately, a microbial suspension wherein the oxidizing agent was not added was also prepared in the same manner. The microbial suspension was stirred for 15 minutes at a temperature shown in Table 6. The amount of formed acrylamide per unit dry weight of the microorganism was determined in the same manner as in Example 3. Assuming that the amount of acrylamide formed per unit dry weight of the microorganism in the suspension stirred at a temperature of 20° C. in the absence of the oxidizing agent is 1, the amounts of acrylamide formed in Examples 19 to 21 are shown as relative values in Table 5.

TABLE 5

| | REAGENT | TEMPERATURE OF THE SUSPENSION (° C.) | AMOUNT OF ACRYLAMIDE FORMED (RELATIVE VALUE) |
|---|---|---|---|
| | NOT ADDED | 20 | 1.0 |
| EXAMPLE 19 | POTASSIUM FERRICYANIDE | 0 | 3.2 |
| EXAMPLE 20 | POTASSIUM FERRICYANIDE | 20 | 2.9 |
| EXAMPLE 21 | POTASSIUM FERRICYANIDE | 60 | 1.4 |

The present invention can not only easily maintain the nitrile hydratase activity of a nitrile hydratase-containing cell or a treated material of the cell under conditions where the cell does not grow, but also improve the nitrile hydratase activity of a nitrile hydratase-containing cell whose activity was once reduced or a treated material of the cell, and thus the present invention is industrially advantageous.

What is claimed is:

1. A method of maintaining or improving a nitrile hydratase activity, which comprises bringing a nitrile hydratase-containing cell or a treated material of the nitrile hydratase-containing cell into contact with an oxidizing agent under conditions where the nitrile hydratase-containing cell does not grow,
   wherein the nitrile hydratase-containing cell is a genetically engineered *Escherichia coli*, and
   wherein a host of the genetically engineered *Escherichia coli* is W3110 strain (ATCC27325), HB101 strain (ATCC33694), JM109 strain (ATCC53223) or WA802 strain (ATCC33526), each of which is derived from *Escherichia coli* K-12.

2. A method of producing an amide compound from a nitrile compound, which comprises contacting a nitrile compound with the nitrile hydratase-containing cell or a treated material of the cell obtained by the method claimed in claim 1 under conditions to produce an amide compound.

* * * * *

UNITED STATES PATENT AND TRADEMARK OFFICE
CERTIFICATE OF CORRECTION

PATENT NO.         : 7,244,595 B2                                      Page 1 of 1
APPLICATION NO. : 10/850374
DATED              : July 17, 2007
INVENTOR(S)        : Yoshikazu Uehara et al.

It is certified that error appears in the above-identified patent and that said Letters Patent is hereby corrected as shown below:

Title page item 56
Under the heading "Other Publications", please change "...nitrile hydrates family" to --...nitrile hydratase family--; and correct "Nov. 20001" to --Nov. 2001--.

Signed and Sealed this

Eighth Day of January, 2008

JON W. DUDAS
*Director of the United States Patent and Trademark Office*